United States Patent [19]

Lopez

[11] Patent Number: 4,494,254

[45] Date of Patent: Jan. 22, 1985

[54] INTRAOCULAR LENS

[76] Inventor: Osvaldo Lopez, 2765 Greenwood Rd., Northbrook, Ill. 60062

[21] Appl. No.: 373,860

[22] Filed: May 3, 1982

[51] Int. Cl.³ .............................. A61F 1/16; A61F 1/24
[52] U.S. Cl. ........................................................... 3/13
[58] Field of Search .............................................. 3/13, 1

[56] References Cited

U.S. PATENT DOCUMENTS

| 4,159,546 | 7/1979 | Shearing | 3/13 |
| 4,174,543 | 11/1979 | Kelman | 3/13 |
| 4,363,143 | 12/1982 | Callahan | 3/13 |
| 4,402,579 | 9/1983 | Poler | 3/13 |

FOREIGN PATENT DOCUMENTS

| 667206 | 6/1979 | U.S.S.R. | 3/13 |

OTHER PUBLICATIONS

The Lindstrom Centrex Style 20 Posterior Chamber Lens (Advertisement), Surgidev Corp., Santa Barbara, Calif., 4 pages, Jan. 4, 1981.

Primary Examiner—Ronald L. Frinks
Attorney, Agent, or Firm—Thomas W. Tolpin

[57] ABSTRACT

An intraocular lens is provided with a specially configured loop which firmly holds the lens element in its desired optical position in the posterior chamber of the eye after extracapsular cataract extraction. The specially configured loop is specially designed to conform to the capsular bag or ciliary sulcus to prevent the lens element from accidentally tilting and to enhance patient comfort.

7 Claims, 6 Drawing Figures

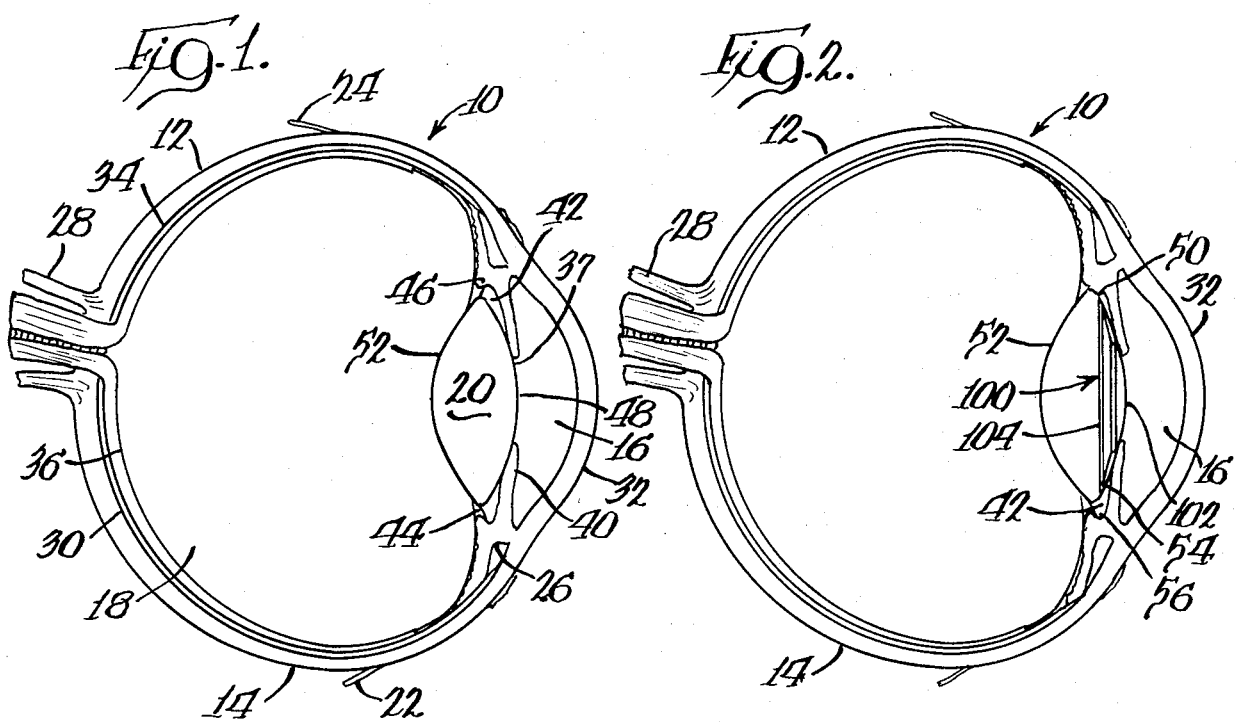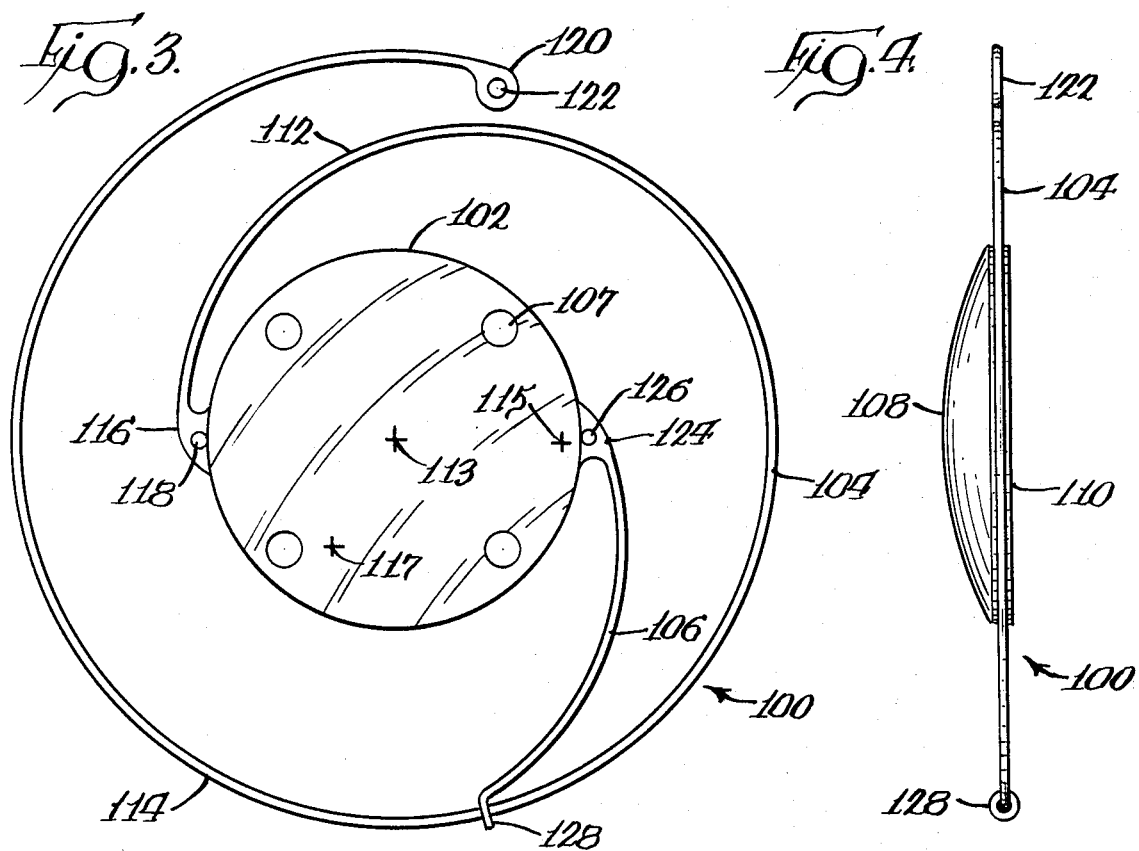

INTRAOCULAR LENS

BACKGROUND OF THE INVENTION

This invention relates to cataract extraction and lens implants, and more particularly, to an intraocular lens implanted in the capsular bag or ciliary sulcus after extracapsular cataract extraction.

Intraocular lenses are used to restore vision in patients whose cataracts have been extracted. A cataract is an opacity or the loss of transparancy of the crystalline lens of the eye. The opacity may be minimal in size and faint in density so that the transmission of light is not appreciably affected, or it may be large and opaque so that light cannot gain entry into the interior of the eye. A cataract is removed if it endangers the health of the eye or seriously impairs the patient's ability to function. Usually a cataract is not removed for visual purposes until the vision in the better eye has deteriorated to at least 20/50.

In a cataract operation, the lens is removed to extract the cataract from the eye. The lens may be removed from the eye by (1) an intracapsular cataract extraction which consists of complete removal of the lens within its capsule through a superior limbal incision, and (2) an extracapsular cataract extraction in which the lens and center portion of the anterior capsule are removed, leaving the capsular bag, i.e. the posterior capsule and remnants (folds) of the anterior capsule. In an extracapsular operation, a superior limbal incision is also made, the anterior portion of the capsule is ruptured and removed, the nucleus is extracted, and the lens cortex is either irrigated or aspirated from the eye. Some patients develop a secondary opacity of the posterior capsule which requires discission. The extracapsular operation is preferred in older patients to reduce long term postoperative vitreous and retinal complications. Extracapsular operations are also very useful for patients with high myopia and retinal degeneration, or previous retinal detachment in the same eye. The extracapsular method is also preferred for individuals under 30 years of age, including children with congenital cataracts. The extracapsular method is particularly adapted to the eye of the young patient because the nucleus of the lens is soft.

Extracapsular cataract extraction is best done when a cataract is complete or mature (ripe). In such lenses the cortex is degenerative and fluid, and is readily irrigated from the eye after the hard nucleus is removed first, usually by external pressure upon the eyeball. If the cataract is incipient or immature, the lens cortex is viscid and tenacious, and significant amounts of it may remain adhered to the retained posterior lens capsule which can cause severe inflammatory reactions. Diseased lenses with cataracts are removed through a small incision at the edge of the cornea.

When the natural lens has been removed in accordance with extracapsular cataract extraction, unfocused light reaches the retina and causes blurring, and postoperative eyeglasses not only magnify greatly but provide little side vision. Intraocular lenses reduce the magnification markedly and widen the field of vision. Intraocular lenses are particularly helpful for patients who cannot insert and remove contact lenses by themselves, such as victims of rheumatoid arthritis and Parkinson's disease and some children. Intraocular lenses also usually provide better binocular vision and causes less aniseikonia than contact lenses.

Most surgeons prefer to perform a cataract extraction and insert the intraocular lens during the same procedure. The intraocular lens is placed into the anterior chamber, aligned with the optical portion of the eye, and wedged in the pupillary aperture. Two types of artificial lenses commonly used are the iris fixation type, which usually results in a square pupil, and the iridocapsular fixation type, which uses the iris and the posterior lens capsule.

Over the years numerous intraocular lenses have been developed. Many of these prior art intraocular lenses, however, are unstable, ineffective, easily dislodgable, dislocate, or change positions, causing discomfort, blurriness, optical misalignment or secondary glaucoma. Typifying some of the many intraocular lenses that have been suggested are those found in U.S. Pat. Nos. 4,315,336; 4,315,337; 4,316,291; 4,316,292 and 4,316,293.

It is therefore desirable to provide an intraocular lens which overcomes most, if not all, of the preceding problems.

SUMMARY OF THE INVENTION

An improved intraocular lens is provided which effectively improves vision for patients who undergo extracapsular cataract extraction. The intraocular lens is specially designed to be implanted in the posterior chamber of the eye, preferably in the capsular bag or in the ciliary sulcus. The novel intraocular lens is stable, optically stationary, reliable and easily implanted during extracapsular cataract extraction, or thereafter, by an experienced surgeon.

The novel intraocular lens has a lens element or optic which is optically positioned and stabilized by a uniformly compressible loop. The loop is specially configured to form an arcuate engagement surface or arc of contact which snugly, but comfortably, fits against and resiliently conforms to the contour of the capsular bag or ciliary sulcus of the patient to prevent the lens element from tilting or accidentally becoming dislodged. The arc of contact is at least 300, and preferably at least 360 degrees. The loop has suture holes or they could be absent.

Desirably, the specially configured loop is comprised of an arcuate, convoluted or loop-like stabilizing element and an optional arcuate strut which is smaller than or the same size as the stabilizing element. The stabilizing element and strut can extend clockwise or counterclockwise in the same or opposite directions. In the preferred form, the stabilizing element extends clockwise for about 480 degrees and the optional strut is located diametrically opposite the stabilizing element and extends clockwise for about 75 degrees. In another form, the stabilizing element extends clockwise for about 540 degrees. In a further form, the stabilizing element and strut are generally comet shaped with the stabilizing element extending clockwise for slightly less than 180 degrees and the strut extending counterclockwise for slightly less than 180 degrees from a position near the stabilizing element. Stabilizing elements and struts having other angular lengths and relationships can also be used to form the loop.

The lens element can be convex, concave, or plano convex or concave with the convexity or concavity implanted either forward or backward. Desirably, the lens element and loop are made of the same or a compatable optical, medical grade plastic, such as polymethylmethacrylate (PMMA) or polypropylene (Prolene).

A more detailed explanation of the invention is provided in the following description and appended claims taken in conjunction with the accompanying drawings.

BRIEF DESCRIPTION OF THE DRAWINGS

FIG. 1 is a cross-sectional view of the eye before extracapsular cataract extraction;

FIG. 2 is a cross-sectional view of the eye after extracapsular cataract extraction with an implanted intraocular lens in accordance with principles of the present invention;

FIG. 3 is an enlarged front view of the intraocular lens;

FIG. 4 is a side view of the intraocular lens;

DETAILED DESCRIPTION OF THE PREFERRED EMBODIMENT

Figure 5:
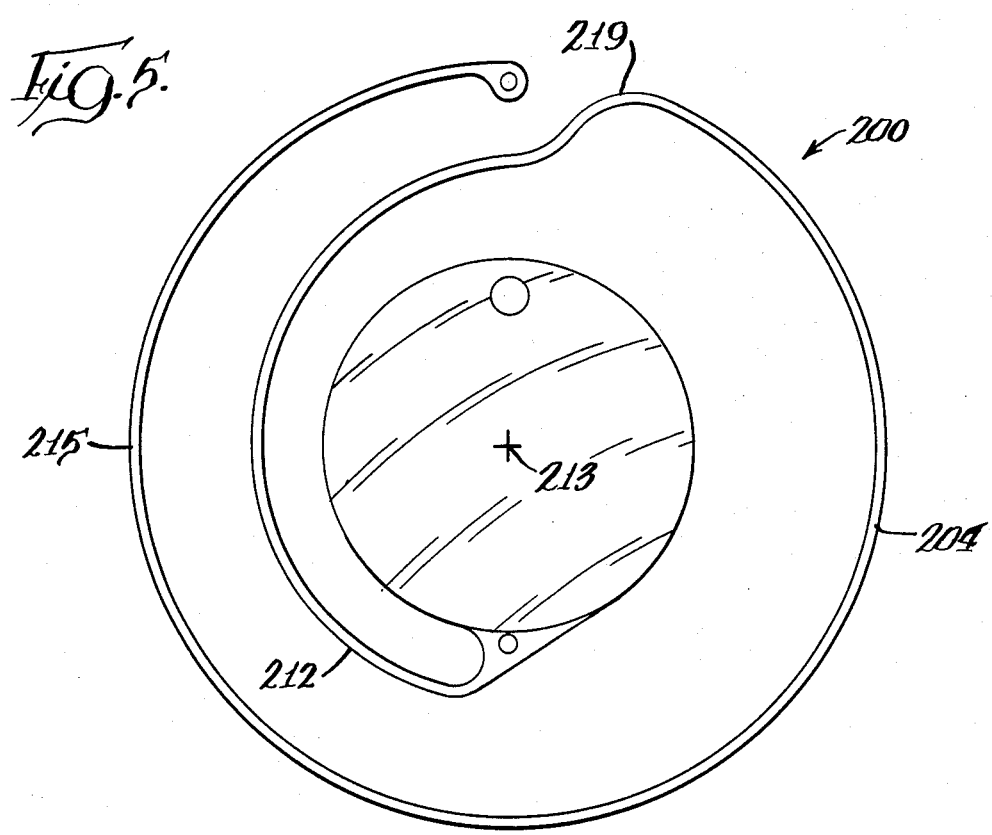
FIG. 5 is a front view of another intraocular lens in accordance with principles of the present invention.

In order to best understand and appreciate the invention, it is best to first have a basic understanding of the physiological components of the eye 10 before and after extracapsular cataract extraction, as shown in FIGS. 1 and 2, respectively. The eyeball 12 is basically a hollow sphere, the walls 14 of which are made of a fairly tough but flexible tissue. The anterior chamber 16 of the eye provides a space or cavity which is located between the cornea 32 and the crystalline lens 20 (FIG. 1). The anterior chamber 16 is bounded in back by the lens 20 and iris 40. The anterior chamber 16 of the eye contains a physiologic fluid while the vitreous humor 18 located behind the lens 20 contains a combination fluid-gel.

The eyeball 12 itself is located within a rigid bony socket and is surrounded by soft tissues and fat. Attached to the eyeball are major muscles 22 and 24 (and others not shown), nerves 28 and blood vessels 30. The muscles control the movement of the eye. These muscles include the lateral rectus muscle 24, the medial rectus muscle 22, the superior rectus muscle, the inferior and superior oblique muscles and tendon, and the inferior rectus muscle. The arteries of the eye include the short ciliary, the long ciliary and the anterior ciliary, as well as the central artery of the retina 36. The nerves attached to the eye include the optic nerve 28 as well as the long and short ciliary nerves. Posteriorly, the fibers of the optic nerve 28 enter through small perforations in the lamina cribrosa. The eyeball or oculus 12 is generally sphere-shaped with coats: the sclera 14 or external coat, which is white and fibrous, the cornea 32 in front, the choroid 34 and the retina 36 or internal coat. The coats are divided into several layers and surround refracting media such as the aqueous humor 37, the crystalline lens 20 and the vitreous humor 18. The aqueous humor 37 is located between the cornea 32 and the lens 20. The vitreous humor 18 is a clear, jelly-like substance containg mucin which fills the space behind the lens 20. The lens 20 is a double convex transparent body between the vitreous and aqueous humors 18 and 37 which is held in place by an elastic capsule and suspensory ligament.

The cornea 32 is comprised of five layers; the endothelial cell layer, Descemet's membrane, stroma, Bowman's membrane and epithelial cells.

The retina 36 or internal coat of the eye is composed chiefly of nerve tissue. The external layer of the retina is composed of terminal nerve cells in the form of rods and cones.

The iris 40 provides a curtain with a central perforation. The pupil is composed of smooth muscular fibers arranged in a circular and radiating manner. The iris varies in color and is suspended in the aqueous humor 37 in front of the lens 20. The iris 40 is surrounded by the ciliary ligament as well as by the ciliary muscle 26 which controls the convexity of the lens 20.

The posterior chamber 42 is bounded anteriorly by the iris 40, posteriorly by the zonule of Zinn 44, inwardly by the crystalline lens 20 and outwardly by the ciliary process and muscle 46.

The crystalline lens 20 is a transparent, biconvex structure or body enclosed in a capsule located directly behind the iris 40 and the pupillary aperture and in front of the vitreous body. The lens is held in position by zonular fibers. Its anterior and posterior surfaces meet at the equator. The center of curvature of the the anterior surface is the anterior pole; the posterior pole is the corresponding point on the posterior surface. The zonular fibers insert into the lens capsule in a zone concentric with the equator and extend further over the anterior than over the posterior surface. The lens 20 continues to form fibers throughout its life. Old fibers become compressed centrally to form an increasingly larger and more inelastic nucleus. Although the crystalline lens appears brilliantly transparent, by microscopic examination it is seen to contain areas of different indexes of refraction and minute opacities, and sometimes mature cataracts.

The crystalline lens 20 is comprised of a lens capsule entirely surrounding the crystalline lens, the epithelium beneath the anterior capsule, a lens substance of newly formed soft layers which provide the cortex, and a dense central area of old fibers which provide the nucleus. The lens capsule is a smooth homogenous, acellular structure. It is thickest on either side of the equator just central to the insertion of the zonular fibers. The capsule is divided into a superficial, thin zonular lamella comprised of acid mucopolysaccharides, which form the attachment of the zonule to the lens, and the cuticular capsule or the capsule proper. The epithelium is located directly under the anterior lens capsule and consists of a single row of cuboidal cells. The nucleus of the lens, comprised of cell processes, is inelastic, yellowish, and increases in size with aging.

The crystalline lens 20 is suspended from the ciliary body around its entire circumference by the zonules of Zinn 44. These delicate but strong fibers hold the lens in place, allowing it to swing like a hammock between the ciliary processes 46. When the eye is at rest, the zonules 44 are taut and exert a pull on the lens capsule that flattens its surface. During accommodation the zonules are relaxed by the contraction of the ciliary muscles. The laxity of the zonules allows the inherently elastic lens capsule to bulge, making the lens more convex. When the zonular fibers rupture, gravity causes the lens to sink and the lens is said to be subluxated. The lens 20 is said to be dislocated when it is found outside the posterior chamber 42, in either the anterior chamber or the vitreous compartment.

In an extracapsular cataract extraction, the crystalline lens 20 and center portion of the anterior capsule 48 are removed leaving a capsular bag 50 (FIG. 2) consisting essentially of the posterior capsule 52 and the remnants or folds 54 of the anterior capsule. The ciliary sulcus 56 is located anteriorly of the capsular bag 50.

After the crystalline lens 20 is removed and the cataracts extracted by extracapsular cataract extraction, an intraocular lens 100 (FIG. 2), sometimes referred to as an artificial crystalline lens, is inserted and placed into the posterior chamber of the eye, preferably in the capsular bag 50 or the cilary sulcus 56. Desirably, the intraocular lens 100 is implanted in the eye in the same procedure as the extracapsular cataract extraction.

In the preferred embodiment of FIGS. 3 and 4, the intraocular lens 100 has a lens element or optic 102, an uniformly compressible, convoluted stabilizing element or loop 104, and an optional auxiliary, uniformly compressible arcuate stabilizing strut or arm 106. In the illustrated embodiment, the optic 102 is a 6 mm circular, plano convex lens with a convex anterior 108 (FIG. 4) and a generally planar or flat posterior 110 with a circular periphery. Optic 102 has one or more instrument-receivable holes or apertures 107 which are engaged by an instrument when inserting or withdrawing the optic from the eye. The power of the lens 102 ranges from 10 to 25 diopters depending on the needs of the particular patient. The intraocular lens can be implanted with the convex anterior 108 facing anteriorly or posteriorly, as desired by the surgeon to fit the needs of the patient. Placing the convexity posteriorly, is believed to reduce iris friction and pupil blockage. The curvature or convexity of the lens 102 is chosen by the opthomologist to enable the patient to see clearly without distortion. Other lens sizes and shapes can be used.

The intraocular lens 100 is made of optical, medical grade plastic which is inert to the fluids of the eye. The lens element 102 is made of a transparent oxygen permeable plastic and/or a impact and scratch resistant plastic, such as polymethylmethacrylate (PMMA). While PMMA is preferred, other lens materials can be used if desired, such as hydrophilic acrylates, polyhydroxyethylmethacrylate (pHEMA), silicone rubber or glass. Loop 104 and strut 106 which are sometimes referred to as "haptics", are made of a flexible, compressible, resilient plastic material such as polypropylene (Prolene) or PMMA, and are elastically shaped and arranged to have rounded ends and curved sides to snugly but comfortably fit inside the eye and cushion against the posterior chamber, capsular bag and ciliary sulcus. Other materials can also be used for the loop and strut, if desired.

The loop is arcuate and rounded and provides a large arc of contact or arcuate engagement surface of at least 300 to 360 degrees that resiliently conforms to the capsular bag and ciliary sulcus. The loop curvature physiologically distributes pressure evenly over a large surface area of the capsular bag or ciliary sulcus to avoid single point pressure which can lead to zonule rupture or ciliary body pressure erosion.

Stabilizing element 104 is generally spiral or helical shaped. The stabilizing element optically stabilizes and prevents tilting of the lens 102 and avoids pupil capture. In the embodiment of FIG. 3, the stabilizing element 104 extends clockwise for about 480 degrees with an inner attached eccentric portion 112 extending eccentrically and progressively outwardly from its point of attachment to the periphery of the lens 102, for about 155 degrees relative to the center 113 of the lens 102, and an outer concentric portion 114 extending at a generally uniform radius from the lens center 113 for about 325 degrees. The center of curvature 115 of the inner eccentric portion 112 is offset from the center 113 of the lens. The center of curvature 117 of the outer concentric portion coincides and is coaxial with the center 113 of the lens. The overall diameter or span of the outer portion 114 of the loop 104 is 12 mm to 13.5 mm with a 0.14 mm thickness. Other sizes and arcuate lengths can be used to accommodate the patient.

As shown in FIG. 4, the loop and strut are generally planar or flat and in coplanar alignment with the base of the lens element as viewed from the side. In some circumstances, it may be desirable that the loop and/or strut extend anteriorly or posteriorly of the lens base.

The inner attached end 116 (FIG. 3) of the loop 104 is cantilevered and bonded or otherwise fixedly secured to the outer edge and tangent of the circular base (periphery) of the lens 102 and can be of an enlarged thickness for strength as well as to define a suture hole 118. The outer unattached, free end 120 of the loop 104 is located arcuately outwardly of the inner attached end 118 and has an enlarged diametric thickness, such as 0.3 mm, which defines another suture hole 122. The loop can have more or less suture holes, with 2 to 4 preferred.

The optional arcuate counterbalance strut 106 extends eccentrically in a spirally or helically clockwise direction from its point of attachment to the lens periphery for about 75 degrees relative to the center 113 of the lens. Strut 106 has a shorter arcuate length than loop 104. The center of curvature 117 of the eccentric strut 106 is offset from the center 113 of the lens. The inner attached end 124 of the strut is cantilevered and bonded or otherwise fixedly secured to the outer edge and tangent of the base (periphery) of the lens 102 at a location diametrically opposite (180 degrees) from the attached end 116 of the loop 104. The inner strut end has an enlarged thickness and defines a suture hole 126. The outer, unattached transverse free end 128 of the strut has an enlarged diametric thickness and can define another suture hole. The outer strut end 128 has the same radius as the outer portion 114 of the loop 104 so that the outer ends 120 and 128 of the loop and strut are spaced equidistant from the center 113 of the lens. Struts having other arcuate lengths can also be used, if desired.

The intraocular lens 200 shown in FIG. 5 is substantially similar to the intraocular lens 100 shown in FIGS. 3 and 4, except the loop or stabilizing element 204 extends clockwise for about 540 degrees with the inner attached portion 212 extending outwardly for about 180 degrees and the outer portion 215 extending outwardly at a generally uniform radius from the lens center 213 for about 360 degrees. A rounded humped portion 219 connects the inner and outer portions. The lens can also have an optional strut.

Figure 6:
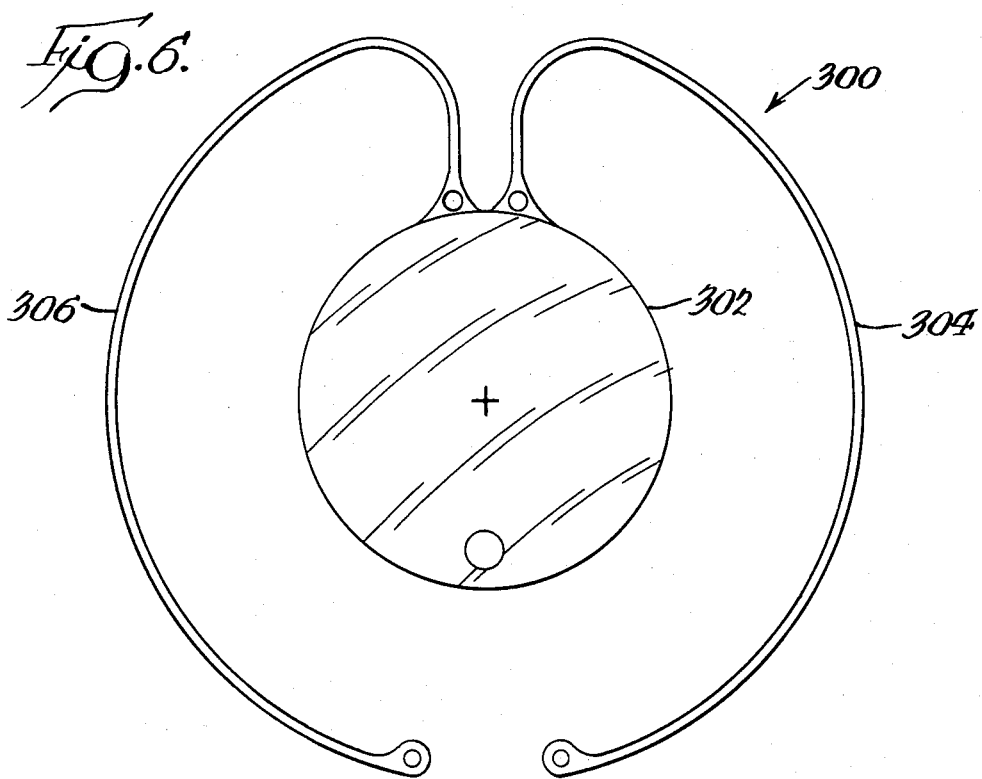
FIG. 6 is a front view of a further intraocular lens in accordance with principles of the present invention.

The intraocular lens 300 shown in FIG. 6 is similar to the intraocular lens 100 shown in FIGS. 3 and 4, except that it is generally comet-shaped with a substantially uniformly compressible convex stabilizing element 304 extending clockwise slightly less than 180 degrees and a substantially uniformly compressible convex strut or stabilizing arm 306 extending counterclockwise for slightly less than 180 degrees from a position near the stabilizing element 304 as viewed from the anterior of the lens element 302. The outer ends of the stabilizing element and strut are positioned equidistant from the center of the lens element 302. The stabilizing element and strut cooperate with each other to provide a generally circular arc of contact or loop that is substantially coplanar with the lens element.

The stabilizing element 304 and strut or arm 306 are symmetrical and each have an inner attached eccentric portion with an inner attached end fixedly secured to the lens element 302. The eccentric portion connects to an outer concentric portion having an outer unattached free end defining at least one suture hole. The outer concentric portions of the stabilizing element 304 and stabilizing arm 306 have a generally uniform radius from the center of the lens element, and the inner attached eccentric portions with attached inner ends are spaced from each other to define an access space therebetween. The outer unattached free ends are spaced from each other and are positioned generally symmetrically opposite the inner attached ends. Thus, the comet-shaped loop means provides a stabilizing element 304 and stabilizing arm 306 each having a flexible arcuate engagement surface of about the same radius for snugly engaging and resiliently conforming to the capsular bag and ciliary sulcus of the patient to fixedly stabilize the lens element in a selected optical position.

The intraocular lens is preferably implanted in the capsular bag or ciliary sulcus during extracapsular cataract extraction. An adult extracapsular cataract extraction can be carried out in a variety of ways, either manually and/or with automated machines, as desired by the surgeon. Typically, extracapsular cataract extraction is performed under general or local anesthesia with the aid of an operating microscope.

For example, after anesthetic induction of the patient, the eye is draped in standard fashion. A lid speculum is inserted and a superior rectus traction suture is placed under the superior rectus tendon. A fornix based conjunctival flap is dissected. The limbus is cleaned with a Gill knife. Hemostasis is controlled with cautery. A continuous corneal scleral groove is made approximately in the 10 to 2 o'clock position along the superior surgical limbus. Two 8-0 silk sutures are preplaced in this partial thickness groove. A 22 gauge disposable needle attached to a TB syringe is then used to create a corneal tract inferiorly in the 6 o'clock meridan. The corneal tract is a full thickness tract entering the anterior chamber. The needle is withdrawn and the anterior chamber is then entered at the 11 o'clock position with a razor blade knife. Afterwards, the cystotome is inserted and a 360 degree anterior capsulotomy is performed while the anterior chamber depth is maintained by a balanced saline solution through a 23 gauge infusion terminal. The anterior capsule is then removed from the eye with fine capsule forceps. The nucleus of the cataract is loosened within its capsule with the cystotome. The corneal section is then enlarged to approximately 160 degrees and the nucleus of the cataract is prolapsed from the anterior chamber. There are various techniques of prolapsing the nucleus of the cataract. Prolapsing can be made easier by the infusion terminal at the 6 o'clock position. The flow of balanced salt solution during prolapsing of the nucleus aids in floating the nucleus out from the anterior chamber.

The two preplaced silk sutures are now tied and the residual cortical material remaining in the eye is aspirated from the anterior chamber with a 3 cc syringe to which is attached a 25 or 27 gauge Olive tipped Cannula. The syringe is managed by the surgeon's two hands giving him complete control over aspiration, as well as reflexing of the aspirated material. Throughout this aspiration, the depth of the anterior chamber is maintained under the surgeon's control utilizing infusion of balanced salt solution. In cases where there is a significant amount of vitreous pressure, it may be necessary to place one or more additional sutures to close the incision in order to prevent excessive outflow of fluid from the anterior chamber. A tight surgical wound during the aspiration irrigation phase of this procedure is actually desirable because it reduces the overall amount of fluid used during this stage of the surgical procedure. It is believed that less damage is suffered by the corneal endothelial cells when the amount of irrigation fluid is reduced. In those cases where closure of the wound fails to maintain proper chamber depth, the rate of infusion can be increased. After all of the residual cortical cataractous material has been aspirated from the eye, the capsular bag and posterior capsule is cleaned and polished, such as with diamond dusted capsule polishing instruments. Afterwards, the anterior chamber is filled with air throught the infusion terminal to displace the salt solution out of the eye.

The intraocular lens which has been previously prepared by soaking it in a balanced salt solution is now ready for insertion. The intraocular lens is implanted through an 8 or 9 mm opening with a large air bubble in the anterior chamber to protect the corneal endothelium. Temporary anterior chamber retaining sutures or wires can provide further protection. The lens and loop can be grasped with a variety of instruments, such as forceps. The intraocular lens is preferably implanted in the center of the capsular bag and need not be rotated. It is important to maintain the normal configuration of the anterior chamber and prevent the delicate corneal endothelial cells on the inside of the cornea from touching the front surface of the intraocular lens during the actual insertion of the intraocular lens. This can be achieved by positive pressure infusion during insertion. By utilizing positive pressure, it is possible to safely insert the intraocular lens even in patients who have high vitreous pressures or whose anterior chambers tend to collapse under surgical entry.

After the intraocular lens has been placed in the proper position, an irridectomy is performed and the corneoscleral incision is closed with sutures. The conjunctiva is likewise sutured closed and the infusion terminal is removed from the corneal tract. The residual air is aspirated with a 30 gauge cannula and replaced with balanced salt solution. The corneal tract is closed with one interrupted 10-0 nylon suture which is removed after 24 hours.

The extracapsular cataract extraction and intraocular lens implant can be performed in a different manner than that described, if the surgeon desires.

Among the many advantages of the inventive intraocular lenses are their:

1. Capability of being implanted in the capsular bag or ciliary sulcus.
2. Uniform compressibility because of the loop.
3. Large arc of contact which conforms to the anatomy of the eye.
4. Excellent horizontal and lateral stability.
5. Ease of implantation without rotation.
6. Ability to be implanted with the convexity either forward or backward.
7. Visual. The lens is closer to the normal location of the crystalline lens of the eye, and most patients will not need additional spectacle correction other than a carrier for their reading segment.
8. Perimetric. There is no loss of side vision as is often the case with heavy lenticular aphakic spectacles.

9. Aniseikonic. Postoperatively there is the least amount of image disparity or magnification. Magnification with intraocular lenses is about 1% to 2% as compared with 35% with aphakic spectacles and 8% to 10% with contact lenses.

10. Psychologic. There is no cosmetic defect as occurs with heavy glasses, nor is there a need for adapting to contact lenses.

11. Treatment of aphakia with the benefits of posterior chamber pseudophakia.

12. Comfort.

13. Reliability.

14. Effectiveness.

Although embodiments of the invention have been shown and described, it is to be understood that various modifications and substitutions as well as rearrangement of parts can be made by those skilled in the art without departing from the novel spirit and scope of this invention.

What is claimed is:

1. An intraocular lens, comprising:
   a lens element;
   a clockwise convex stabilizing element extending clockwise about said lens element for slightly less than 180 degrees;
   a counterclockwise convex stabilizing arm extending counterclockwise about said lens element for slightly less than 180 degrees;
   said stabilizing element and arm each having an attached end engaging and securely attached to said lens element and an unattached free end;
   each of said attached ends and said unattached ends defining a suture hole;
   said attached end of said stabilizing element being spaced from said attached end of said arm; and
   said suture hole in said attached end of said stabilizing element being spaced from said suture hole in said attached end of said arm.

2. An intraocular lens in accordance with claim 1 wherein said free ends of said stabilizing element and arm are positioned generally adjacent each other.

3. An intraocular lens, comprising:
   a transparent lens element selected from the group consisting essentially of polymethylmethacrylate, hydrophilic acrylate, polyhydroxyethylmethacrylate, silicone rubber and glass, said lens element having a periphery and defining a center and at least one instrument-receivable aperture; and
   comet-shaped loop means extending generally about said periphery of said lens element and defining a generally circular arc of contact about said lens element for contacting the posterior chamber of an eye after extracapsular cataract extraction, said comet-shaped loop means comprising symmetrical stabilizers including a clockwise flexible convex stabilizing element and a counterclockwise flexible convex stabilizing arm, said stabilizing element and arm each being of optical medical grade plastic and extending arcuately in different directions from said periphery of said lens element for slightly less than 180 degrees to substantially fixedly stabilize said lens in a selected optical position, said stabilizing element and said arm each having an inner attached end fixedly connected to and engaging said lens element and an outer unattached free end positioned generally symmetrically opposite said inner attached end, and said attached ends being spaced from and cooperating with each other to define an access space therebetween.

4. An intraocular lens, comprising:
   a transparent lens element of optical medical grade plastic for replacing a crystalline lens and improving vision in a patient after extracapsular cataract extraction, said lens element having a convex anterior and a generally planar posterior with a generally circular periphery and defining a center and at least one instrument receivable hole;
   a substantially uniformly compressible stabilizing element of optical medical grade plastic positioned in substantial coplanar alignment with said planar posterior of said transparent lens element, said uniformly compressible stabilizing element having an inner attached eccentric portion with an inner attached end fixedly secured to said lens element and an outer concentric portion with an outer unattached free end, said outer concentric portion of said stabilizing element extending clockwise from said inner attached eccentric portion as viewed from the anterior of said lens element and having a generally uniform radius from said center of said lens element, said outer unattached free end of said stabilizing element being positioned from said inner attached end of said stabilizing element at an angle substantially greater than 120 degrees and defining at least one suture hole:
   a substantially uniformly compressible stabilizing arm of optical medical grade plastic positioned in substantial coplanar alignment with said planar posterior of said lens element, said uniformly compressible stabilizing arm having an inner attached eccentric portion with an inner attached end fixedly secured to said lens element and an outer concentric portion with an outer unattached free end, said inner attached eccentric portion and said inner attached end of said arm being spaced from, but positioned generally adjacent and in proximity to, said inner attached eccentric portion and said inner attached end, respectively, of said stabilizing element and defining an access space therebetween, said outer concentric portion of said arm extending generally counterclockwise from said inner attached portion of said arm as viewed from the anterior of said lens element generally opposite and complementary to said stabilizing element and at a generally uniform radius from said center of said lens element, said outer unattached free end portion of said arm being positioned from said attached end of said arm at an angle substantially greater than 120 degrees and defining at least one suture hole, said stabilizing element and stabilizing arm each having a flexible arcuate engagement surface of about the same radius for snugly engaging and resiliently conforming to the capsular bag and ciliary sulcus of the patient to substantially fixedly stabilize said lens element in a selected optical position.

5. An intraocular lens in accordance with claim 4 wherein said clockwise outer portion of said stabilizing element and said counterclockwise outer portion of said arm each extend for slightly less than 180 degrees.

6. An intraocular lens in accordance with claim 5 wherein said optical medical grade plastic of said lens element, stabilizing arm, and stabilizing element include polymethylmethacrylate and said stabilizing arm and said stabilizing element are integrally connected to said lens element.

7. An intraocular lens in accordance with claim 5 wherein said optical medical grade plastic of said lens element includes polymethylmethacrylate and said optical medical grade plastic of said stabilizing element and stabilizing arm includes polypropylene.

* * * * *